(12) United States Patent
Ahmed

(10) Patent No.: US 6,946,442 B2
(45) Date of Patent: Sep. 20, 2005

(54) METHOD OF HASTENING CERVICAL RIPENING

(76) Inventor: Asif Syed Ahmed, 74 Lordswood Road, Harbrone, Birmingham (GB), B17 9BY ( * ) Notice: Subject to any disclaimer, the term of this patent is extended or adjusted under 35 U.S.C. 154(b) by 488 days.

(21) Appl. No.: 09/952,604

(22) Filed: Sep. 13, 2001

(65) Prior Publication Data

US 2002/0137680 A1 Sep. 26, 2002

Related U.S. Application Data

(63) Continuation-in-part of application No. 08/849,930, filed as application No. PCT/GB95/02801 on Nov. 30, 1995, now abandoned.

(30) Foreign Application Priority Data

Nov. 30, 1994 (GB) .............................................. 9424232

(51) Int. Cl.⁷ ........................ A61K 38/18; C07K 14/475
(52) U.S. Cl. ............................. 514/12; 514/2; 530/399; 530/350
(58) Field of Search ........................ 514/2, 12; 530/399

(56) References Cited

U.S. PATENT DOCUMENTS

| | | |
|---|---|---|
| 4,352,790 A | 10/1982 | Johansson et al. |
| 5,409,955 A | 4/1995 | Bockow et al. |

OTHER PUBLICATIONS

Dong et al. Am. J. Obstet. Gynecol. 177(4): 907–917, 1997.*
Gordon M. Stirrat et al. Prescribing in Pregnancy Clinics in Obstetrics and Gynaecology, Jun. 1986, p. 215–229, vol. 13/No. 2, W.B. Saunders Company, London, Philadelphia, Toronto, XP 000565915.

James A. McGregor et al. Preterm Birth and Infection: Pathogenic Posibilities, American Journal of Reproductive Immunology and Microbiology, Mar. 1988, pp. 123–132 1988 alan R. Liss, Inc. XP 000565913.

A. Ahmed et al, Functional platelet–activating factor receptors linked to inositol lipid hydrolysis, calcium mobilization and tyrosine kinase activity in the human endometrial HEC–1B cell line Journal of Reproduction and Fertility, Jul. 1994, p. 459–466, vol. 101, No. 2, XP 000564921.

Journal of Reproduction and Fertility Abstract Series: No. 14, Dec. 1994. p. 6, XP 0005649 8.

D. Stephen Charnock–Jones et al. Biology of Reproduction, Sep. 1994, p. 524–530, vol. 51, No. 3, XP 000565923.

Abstract of papers to be presented at the Vith Meeting of the Europen Placenta Group Joint Meeting Placenta Sep. 1995, vol. 16, No. 6, p. A42 XP 000564927.

C. Michelet et al. La maturation Artificielle du col gravide par action locale de leucocytes maternels Review Franzaise de Gynecologie et D'obstertrique 1986, pp. 137–138–141 XP 000565914.

* cited by examiner

*Primary Examiner*—Christine J. Saoud
(74) *Attorney, Agent, or Firm*—Gardner Carton & Douglas LLP

(57) ABSTRACT

The use of an agent for controlling vascular permeability within the cervix is disclosed for controlling cervical ripening. To hasten cervical ripening, the agent is one which increases vascular permeability and is selected from $VEGF_{121}$, $VEGF_{145}$, $VEGF_{165}$, $VEGF_{189}$, $VEGF_{206}$, a smaller, active VEGF fragment, and placenta growth factor (PlGF). If cervical ripening is to be delayed, the agent is one which reduces vascular permeability, e.g. a VEGF receptor antagonist or antibody. The agents of the present invention can be used as a means of managing labor.

2 Claims, 14 Drawing Sheets

VEGF

G3PDH

SEQUENCE LISTING

```
<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:vascular
      endothelial growth factor antisense (3') primer

<400> SEQUENCE: 1
tgaaggtcgg agtcaacgga tttggt                                          26

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:vascular
      endothelial growth factor sense (5') primer

<400> SEQUENCE: 2
catgtgggcc atgaggtcca ccac                                            24

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:vascular
      endothelial growth factor sense (5') primer

<400> SEQUENCE: 3
gaaaccatga actttctgct g                                               21

<210> SEQ ID NO 4
<211> LENGTH: 21
<212> TYPE: DNA
<213> ORGANISM: Artificial Sequence
```

```
-continued

<220> FEATURE:
<223> OTHER INFORMATION: Description of Artificial Sequence:vascular
      endothelial growth factor antisense (3') primer

<400> SEQUENCE: 4
tgtatcagtc tttcctggtg a                                             21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:vascular
      endothelial growth factor sense probe

<400> SEQUENCE: 5
ccgcccactg ggtcgtgcca gg                                            22
```

METHOD OF HASTENING CERVICAL RIPENING

This is a continuation-in-part of pending U.S. patent application Ser. No. 08/849,930 filed on Aug. 18, 1997 now abandoned which is a 371 of PCT/GB 95/02801, filed Nov. 30, 1995 and claims foreign priority to U.K. Patent Application Serial No. 9424232.8 filed on Nov. 30, 1994.

TECHNICAL FIELD OF THE INVENTION

This invention relates to growth factor expression in cervical treatment and is more particularly concerned with agents for controlling softening or ripening of the cervix as a means of managing labour either to delay cervical ripening in order to delay delivery or to hasten cervical ripening in order to assist delivery.

BACKGROUND ART

Pre-term birth accounts for about 6–8% of all pregnancies and is responsible for 75% of all perinatal deaths. Currently, pre-term birth can be delayed for a few days by administering a muscle relaxing agent which serves to relax the myometrium. However, there is a need for agents which can delay the onset of labour for longer periods to avoid children being born very prematurely. Additionally, many full term deliveries are made difficult because, whilst there is strong myometrial activity, there is insufficient cervical ripening. Thus, there is a need to be able to control cervical ripening in a similar way to that in which myometrial activity can be controlled so that further control over pre-term and difficult full- or post-term deliveries can be exercised.

The present invention has been made as a result of investigation of the mechanism which leads to ripening of the cervix during pregnancy. The cervix has commonly been regarded as serving a purely passive role in which it softens or ripens during pregnancy to facilitate passage of the foetus during delivery. It is known that prostaglandins and oestrogen have a part to play in the changes in cervical properties which take place during pregnancy, but the mechanism by which they act is poorly understood.

BROAD DISCLOSURE OF THE INVENTION

During our investigation, it has been found that cervical ripening is dependent upon vascular permeability within the cervix.

In one of its aspects, the present invention resides in the use of an agent for controlling vascular permeability within the cervix in the manufacture of a medicament for controlling cervical ripening.

In another of its aspects, the present invention resides in a method of controlling cervical ripening comprising administering to a patient an agent for controlling vascular permeability within the cervix.

In the case where cervical ripening is to be hastened, the agent is one which increases vascular permeability. An example of such an agent is vascular endothelial growth factor (VEGF) which is sometimes referred to as vascular permeability factor (VPF). Our studies have revealed that VEGF mRNA is highly expressed in human cervix and that VEGF peptide is localised around cervical blood vessels, thereby indicating that VEGF plays an important role in cervical ripening.

VEGF, a heparin binding growth factor with a molecular weight of 45 kDa, is a dimeric secreted glycoprotein composed of two identical subunits linked by disulphide bonds which promote vascular endothelial cell growth. Due to the alternative splicing of mRNA, five different molecular species of human VEGF are generated. These VEGFs have 121 amino acids ($VEGF_{121}$), 145 amino acids ($VEGF_{145}$), 165 amino acids ($VEGF_{165}$), 189 amino acids ($VEGF_{189}$) and 206 amino acids ($VEGF_{206}$). (It will be understood that in different species, the VEGF fragments may vary slightly. For example in the murine model, there is a $VEGF_{164}$ fragment rather than a $VEGF_{165}$ fragment.) VEGF exhibits 18% overall sequence homology with platelet-derived growth factor and 53% sequence homology with placenta growth factor (PlGF). VEGF is not only a powerful mitogen for endothelial cells, but also mediates a number of other endothelial effects, including secretion of collagenase IV, nitric oxide (NO), urokinase-type plasminogen activating factors and PAI-1. In addition to the endothelial mitogenic capacity of the VEGF family, $VEGF_{189}$ is known to induce fluid and protein extravasation from blood vessels. On a molar basis, VEGF is $5\times10^3$ times more potent than histamine at increasing vascular permeability. Whilst there is evidence that VEGF is present in the ovary, in human endometrium and in human placenta, as far as we are aware it has never previously been identified in the cervix.

The agent for hastening cervical ripening may be $VEGF_{121}$, $VEGF_{145}$, $VEGF_{165}$, $VEGF_{189}$ and/or $VEGF_{206}$, or a smaller, active VEGF fragment, or another compound of the VEGF family, eg PlGF. PlGF is available from R & D Systems Ltd, Nottingham, GB.

Another example of an agent for hastening cervical ripening is platelet-activating factor (PAF) or a stable analog of PAF such as N-methylcarbamylPAF or agents that inhibit its breakdown such as inhibitors of PAF acetylhydrolase, the enzyme that breaks down PAF.

Platelet-activating factor (PAF) is an inflammatory mediator that increases vascular permeability. It induces bronchoconstriction and its receptor antagonist WEB 2086 as an aerosol spray blocks bronchoconstriction and fall in systemic blood pressure. In reproductive terms, PAF antagonists inhibit implantation in the mouse and rat. PAF is also produced by stromal cells of human endometrium, where its levels are hormonally regulated. PAF act on glandular epithelium to release prostaglandins in vitro. Addition of PAF to culture medium increases the metabolic rate, cleavage rate and implantation potential of mouse. PAF has also been shown to increase the production and release of $PGE_2$ from decidual cells.

It has been found that VEGF increases connexin-43 and so may be used in the manufacture of medicament for promoting labour by increasing connexin-43. This is described hereinafter in greater detail. Thus, VEGF may be administered concomitantly with oxytocin, especially in cases where myometrial contractility is weak, to promote labour.

In the case where cervical ripening is to be delayed, the agent is one which reduces vascular permeability. Such an agent may be selected from VEGF receptor antagonists, VEGF receptor antibodies, agents which decrease the expression of VEGF, agents which neutralise the effect of VEGF, PlGF receptor antagonists, PlGF receptor antibodies, agents which decrease the expression of PlGF, and agents which neutralise the effect of PlGF.

The body also produces endogenous soluble receptors for VEGF such as in the case of fibroblast growth factor (FGF). These soluble VEGF receptors, such as kinase domain receptor (KDR/flk-1) and flt-1 (fms-like tyrosine kinase) receptor will block the effect of VEGF and can serve as antagonists in delaying labour.

It is considered that suitable VEGF receptor antagonists can be found amongst the antibodies raised against VEGF. The following serve as examples:—

VEGF mAb A4.6,1 Genentech, USA (Growth Factors 7:53–64, 1992).
VEGF (A-20) sc-152 (Santa Cruz Biotechnology, USA)
flt (C-17) sc-316 (Santa Cruz Biotechnology, USA)
flk-1 (C-20) sc-315 (Santa Cruz Biotechnology, USA)
flt-4 (C-20) sc-321 (Santa Cruz Biotechnology, USA)
PlGF antibody The agent for delaying cervical ripening may be selected from PAF receptor antagonists, PAF receptor antibodies, agents which will breakdown PAF, agents which decrease the expression of PAF, agents which neutralise the effect of PAF.

PAF receptor antagonists, e.g., WEB 2086, WEB 2170, BN52021 and CV-3988 amongst others, have been proposed for the treatment of asthma, but as far as we are aware, the use of such antagonists for controlling labour has never been previously proposed.

We have found that high levels of mRNA for PAF-R are expressed in the epithelial cells lining the crypts and around the cervical blood vessels in pregnant cervix, whereas very low levels of mRNA are found in non-pregnant cervix. This finding leaves us to believe that the cervix serves an active role during pregnancy and labour and that PAF receptor antagonists can be used to delay the onset of labour.

Human recombinant platelet-activating factor acetylhydrolase is an agent which will breakdown PAF and is therefore considered potentially useful for delaying the onset of labour, as are antisense oligonucleotides which block PAF or PAF receptor expression.

Antisense oligonucleotides which block VEGF expression, or P1GF expression or VEGF/PlGF receptors are also considered to be suitable for delaying cervical ripening.

Bradykinin $B_2$ receptor antagonists such as Hoe-140 (Hoechst AG, Germany) and histamine receptor antagonists may also delay labour.

BRIEF DESCRIPTION Of THE DRAWINGS

The present invention will now be described in further detail and with reference to the accompanying drawings, in which:—

DETAILED DESCRIPTION OF THE INVENTION

Materials and Methods

Tissue Collection and Process

Figure 1:
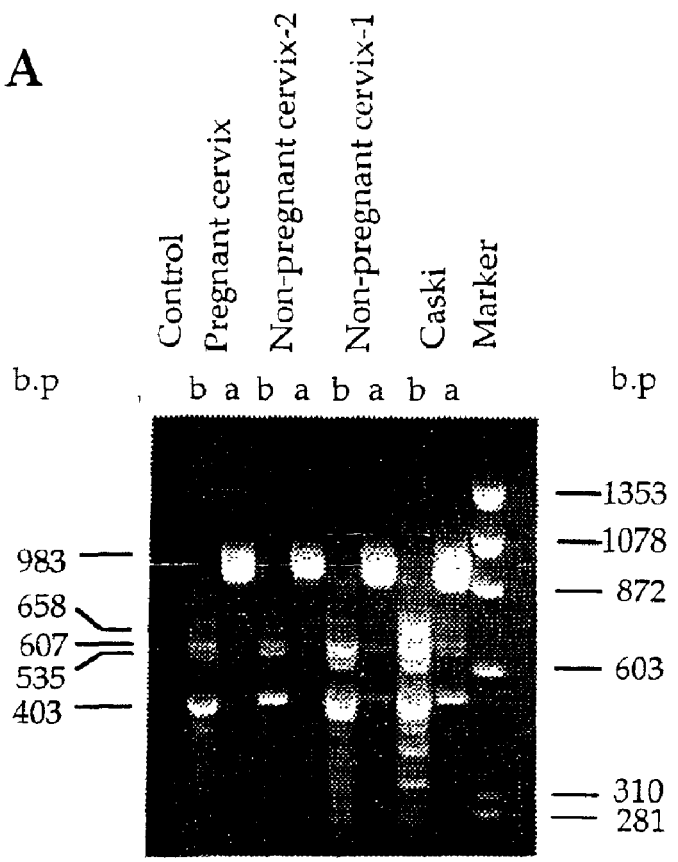
FIG. 1A shows products separated by agarose gel electrophoresis of reverse transcriptase-polymerase chain reaction (RT-PCR) amplification of cDNA generated from various cervical tissue samples.
FIGS. 1B and 1C are autoradiographic pictures of amplified products shown in FIG. 1 which have been hybridised with a VEGF-specific probe (FIG. 1B) or a G3PDH specific probe (FIG. 1C) labelled with $\gamma^{32}$ P ATP.
Figure 1:
Figure 1:

Full thickness cervical biopsies were collected from women of reproductive age undergoing hysterectomy for the investigation of subjective menorrhagia (non-pregnant) and gravid hysterectomy (pregnant cervix). Tissue obtained from such women was shown to be histologically normal. For immunohistochemical studies, the tissue was rinsed in sterile saline and immediately immersed in 10% formaldehyde and processed for paraffin wax embedding. A human cervical carcinoma epithelial cell line, Caski, was also used in these studies.

For immunohistochemical studies, the tissue was rinsed in sterile saline and immediately immersed in 10% formaldehyde and processed for paraffin wax embedding. For RT-PCR studies, total RNA was extracted from 200 mg of frozen pieces of cervical tissue and from one flask of Caski cells, by the RNAzol B method (AMS Biotechnology, Witney, Oxon, UK). Briefly, tissue was homogenised in a buffer containing RNAzol and total RNA was extracted by a single step procedure of the acid-guanidinium thiocyanate-phenol-chloroform method (Chomczynski and Sarchi, Analytical Biochem., 162:156–159, 1987). For in situ hybridization studies, frozen tissues were surrounded in embedding medium (OCT compound, Miles Scientific) before 10 $\mu$m sections were cut using a cryostat (−15 to −19° C.) and thaw mounted onto poly-L-lysine (Sigma, Poole, U.K.) coated glass slides. Section were stored (less than 2 weeks) at −70° C. until being prepared for in situ hybridization.

Pre-Capillary Quantitation Study in Human Non-Pregnant Cervix

The aim of the research was to quantify the pre-capillary density in four histological differentiated parts of the human uterine non-pregnant cervix. The pre-capillary density in four histological differentiated parts of the cervix was measured with a microscope in serial 5$\mu$m tissue sections obtained from cone biopsies fixed in formalin and embedded in paraffin wax. The sections stained with QBend10 using the ABC/HRP labelling method. The pre-capillary density was taken at an objective magnification of ×10. The parts of the uterine cervix to be examined quantitatively were established as follows:—

(a) the side margins corresponding to the area of stroma just underneath the squamous epithelium;
(b) the one just underneath the columnar epithelium;
(c) the deep margin corresponding to a deep stroma area; and
(d) the margin corresponding to the transformation zone of the uterine cervix.

Since the QBend10 itself stains the endothelial lining, the boundaries external to this in each single capillary were hand-drawn interactively on a defined dimensions area on a paper.

RT-PCR cDNA was synthesised according to the manufacturer's instructions by using a cDNA Cycle Kit (Invitrogen) which makes use of AMV reverse transcriptase to generate high yields of full-length first-strand cDNA from RNA for use as a template in polymerase chain reaction (PCR) amplifications. After first strand synthesis, 10% of the reverse transcriptase reaction was added to 10 mM Tris-HCl, pH 8.8, 1.5 mM $MgCl_2$, 50 mM KCl, 0.1% v/v Triton-X100, 125 mM dNTPs, 1 mM of each primer and DynaZyme Thermostable DNA Polymerase (2U; Finnzyme Oy Espoo, Finland). Antisense VEGF primer or Oligo-dT primer was used for priming the RNA. The internal standard for quantifying gene expression was glyceraldehyde 3-phosphate dehydrogenase (G3PDH). The sequence of the primers used in this study are shown below.

```
G3PDH:
Sense (5') primer: 5' TGAAGGTCGGAGTCAACGGATTTGGT 3'-SEQ ID NO: 1
Antisense (3') primer: 5' CATGTGGGCCATGAGGTCCACCAC 3'-SEQ ID NO: 2

VEGF
Sense (5') primer: 5' GAAACCATGAACTTTCTGCTG 3'-SEQ ID NO: 3
Antisense (3') primer: 3' TGTATCAGTCTTTCCTGGTGA 3'-SEQ ID NO: 4
```

Amplification cycles were 1 min at 95° C., 2 min at 55° C. and 3 min at 72° C. in a 480 Perkin Elmer Cetus DNA Thermal Cycler. The amplified products were separated by 1.2% agarose gel electrophoresis (FIG. 1A) and transferred to a positively charged Hybond-$N^+$ membrane by one hour downward capillary transfer (Chomczynski and Sarchi, Analytical Biochem.,201:134–139, 1992) and hybridised with a VEGF specific probe (FIG. 1B) and a G3PDH probe (FIG. 1C) labelled with $\beta^{32}P$ ATP. Hybridisation was performed overnight at 42° C. in 6×Net, 5×Denhart's, 0.5% Nominet P-40, 10% Dextran and 100 mg/ml heat-denatured salmon sperm DNA. The hybridised membrane was washed to a final stringency of 2×SSC (standard saline citrate) and 0.1% SDS (sodium dodecyl sulphate) at 42° C. and exposed to autoradiography at −70° C. for 1 day.

In situ Hybridization

Pre-treatment of Sections

The poly-L-lysine coated sections were fixed in 4% paraformaldehyde in PBS (pH 7.4) for 5 min, acetylated in 0.1 M triethanolamine (TEA), pH 8.0, with acetic anhydride (0.25% w/v) for 10 minutes. Slides were dehydrated through an ascending graded series of alcohol (70%, 80%, 95% and 100% v/v) followed by incubation in chloroform for 5 min. The sections were then partially rehydrated sequentially in 100% (v/v) and 95% (v/v) ethanol and air dried. As a control for non-specific binding, before fixation, some sections were treated with 100$\mu$gm/ml of RNAse A (Sigma, Poole, U.K.) for 1 hour at 37° C.

Preparation of Probes

VEGF Probe: The probe for VEGF was a synthetic oligonucleotide probe directed against human VEGK cDNA (22 bases directed against base pairs 874 to 853 of human VEGF cDNA CCG CCC ACT GGG TCG TGC CAG G-SEQ ID NO:5) which had been tail-labelled with [$^{35}S$] dATP for in situ hybridization by 3' terminal deoxynucleotidyl transferase using a commercial available kit (NEN—DuPont). As a control, the sense probe (containing the same sequence as the human VEGF cDNA) was also end labelled with [$^{35}S$] dATP by the same method as above.

Hybridisation: Following acetylation, the air dried slides were hybridised in a moist chamber under coverslips in a hybridization buffer containing formamide (50% v/v), 3 M NaCl, 0.3 M Na citrate, 0 1 mM EDTA, dextran sulphate (10% w/v), 0.5 ml Denhardt's reagent, 100$\mu$gm/ml of salmon sperm DNA, 100 μgm/ml of yeast transfer RNA, 100 μgm/ml of polyadenylic acid A and 1×10⁶ d.p.m. /ml of $^{35}$S labelled sense or antisense RNA probe. The sections were covered with a paraffin coverslip and hybridisation was carried out in a moist chamber at 50° C. for 16 hours. Following hybridisation, the coverslips were removed in a large volume of 1×SSC, the sections were then washed three times in 1×SSC at wash temperature for 20 minutes, then twice for 60 minutes at room temperature and briefly rinsed in distilled water. At least three consecutive sections were used for hybridization from each cervix, two were labelled with the antisense probe and one was with the sense probe. Autoradiography was carried out by coating the slides in Ilford K5 emulsion (Ilford Ltd. Cheshire, UK). Following dilution of the emulsion (1:1) in distilled water with 2% (v/v) glycerol, the slides were dipped in the emulsion, dried on the bench for at least two hours and the dry slides were stored in a light-proof box containing silica gel at 4° C. for 3 weeks. The sections were then stained lightly with 0.1% cresyl violet and mounted.

PAF-R Probe: For the generation of human PAF-R specific probes, the plasmids were linearized with Hind III or Bam HI and the transcripts were generated, by [$^{35}$S]-UTP (1500 Ci mmol$^{-1}$, Dupont NEN) incorporation using the T7 or T3 RNA polymerase, respectively. The probes thus generated were single stranded RNA probes, and had a specific activity of 1×10⁷ dpm per microgram of plasmid template.

Hybridization: Following acetylation, the air dried slides were hybridised in a moist chamber under coverslips in the hybridization buffer containing formamide (50% v/v), 3 M NaCl, 0.3 M Na citrate, 01 mM EDTA, dextran sulphate (10% w/v), 0.5 ml Denhardt's reagent, 100μgm/ml of salmon sperm DNA, 100 μgm/ml of yeast transfer RNA, 100 μgm/ml of polyadenylic acid A and 1×106 d.p.m./ml of $^{35}$S labelled sense or antisense RNA probe. Hybridisation was carried out at 50° C. for 16 hours. The slides were then washed in 4× standard saline citrate (SSC) and then treated with 20 μg/ml RNAse A (Sigma, Poole, UK.) for 20 minutes at 37° C. in 0.5 M NaCl, 10 mM Tris pH 7.0, 1 mM EDTA. This was followed by washes of increasing SSC stringency. The slides were washed twice in 2×SSC with 1 M dithiotheritol (DTT) for 10 minute at room temperature followed by 1×SSC with 1 M DTT for 20 minutes, and then washed at 0.5×SSC with 1 M DTT for 20 minutes, and finally in 0.1×SSC with 1 M DTT for 60 minutes at 65° C. and dehydrated in an ethanol series.

Immunocytochemistry

Serial 3 μm sections of formalin-fixed, paraffin-embedded tissue prepared as described above were used for immunohistochemistry. These sections were de-paraffinized by incubation for 5 min with Histoclear and hydrated in methanol, and endogenous peroxidase activity was quenched by the addition of 0.3% (v/v) of hydrogen peroxide for 10 minutes. The primary antibody was a rabbit polyclonal antibody raised against the human VEGF and was purchased from Peninsula Laboratories, Merseyside, UK. It is highly specific but cross reacts completely with human VEGF. Non-immune goat serum (10% in 0.05 mol/l PBS) was used as a dilution of the primary antibody to reduce non-specific binding. Amplification of the primary antibody reaction was achieved using a goat anti-rabbit secondary antibody (diluted 1:200 in 0.05 mol/l PBS, pH 7.4) for 30 min followed by a complex of streptavidin (Dako Ltd, Bucks, UK) and biotinylated peroxidase (Dako Ltd, Bucks, UK). Finally, the binding was visualised by the addition of 0.5 mg/ml diaminobenzidine (Sigma Chemical Co. Ltd, Poole, Dorset, UK) and 0.01% hydrogen peroxide in 0.05 mmol/l PBS to the antigen-antibody complex. Between each step, the sections were washed in 3×200 ml of 0.1% (v/v) polyoxylene-10-oleoyl-ether in 0.05 mmol/l PBS over a period of 15 min. All incubations of antisera were carried out at a room temperature in a wet chamber mounted on a rocking tray which ensures a movement of antiserum over the whole section. Then the sections were counter-stained with Mayers Haematoxylin, dehydrated and mounted.

To test the specificity of the immunohistochemical staining, the primary antibody was omitted from the sections, or replaced with goat non-immune serum in control experiments.

Results and Discussion

Quantitation of Pre-capillary Staining in Human Non-pregnant Cervix

The following table shows the results of the quantitative evaluation of the capillary density in the stroma of the uterine cervix:—

| AREA OF CERVIX | CAPILLARY DENSITY (c/mm³) |
|---|---|
| Squamous epithelium | 13 |
| Deep stroma | 11 |
| Transformation zone | 4 |
| Columnar epithelium | 3 |

In the stroma area underneath the squamous epithelium, the value of the capillary density or number of capillaries per square mm is 13. Similar capillary density values (11) can also be seen in the deep layers of stroma. The values corresponding to capillary density become lower though, from the area of stroma close to the transformation zone (4) up to the area of stroma close to the columnar epithelium (3). These areas of stroma having the lowest capillary density values were shown to have a high density of crypts.

VEGF mRNA Expression

Total RNA from non-pregnant cervix was reverse transcribed and subjected to 30 rounds of amplification of PCR using VEGF sense and an antisense oligonucleotide primer shared by all differentially spliced VEGF mRNA species. Hybridisation using an antisense VEGF probe showed that the amplified species, identified in all tissues examined, were 403, 535, 607 and 658 bp fragments corresponding to the mRNA encoding $VEGF_{121}$, $VEGF_{165}$, $VEGF_{189}$ and $VEGF_{206}$, respectively (FIG. 1B). However, the transcript corresponding to $VEGF_{206}$ was shown to exist in lower amounts, while the $VEGF_{121}$ transcript was found to exist in higher amounts among the other VEGF transcripts in each one of the samples tested. A control reaction without input cDNA gave no product, thus eliminating the possibility of contamination. The cervical carcinoma cell line was also found to express the same four transcripts of VEGF mRNA.

VEGF mRNA Localization

Figure 2:
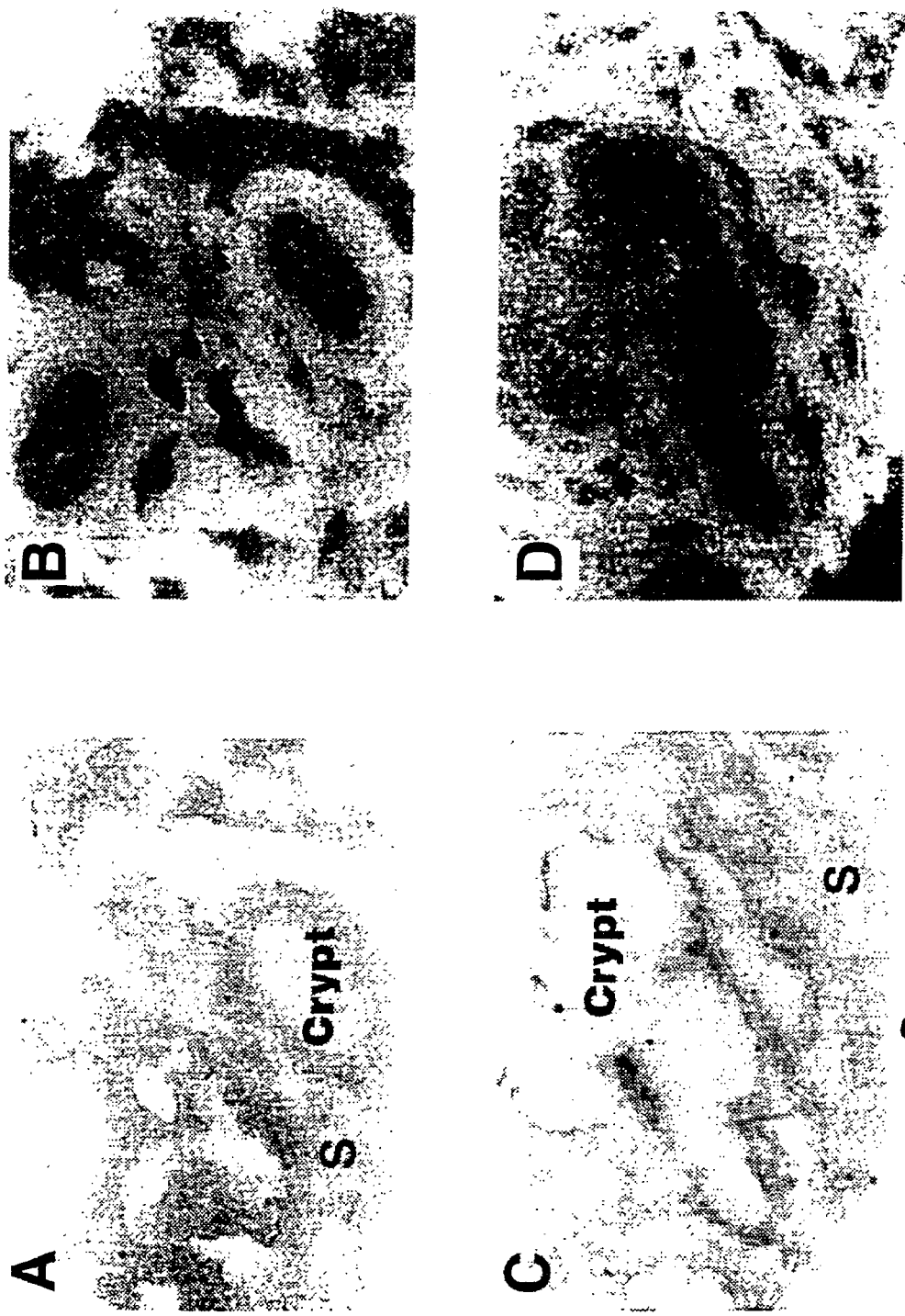
FIGS. 2A and 2B are respectively light and dark field autoradiographs showing the expression of VEGF mRNA in the basal laminar of crypts in a cervical tissue sample.
FIGS. 2C and 2D are respectively light and dark field autoradiographs showing the expression of VEGF mRNA in the periglandual stroma in a cervical tissue sample.

In order to identify the site of expression of VEGF mRNA, in situ hybridisation was carried out on samples of cervix. The expression of VEGF mRNA was demonstrated in the basal laminar of crypts and in the periglandual stroma (FIG. 2). There was an apparent lack of hybridisation signal in the epithelial cells of the crypts.

VEGF peptide Localization

Figure 3:
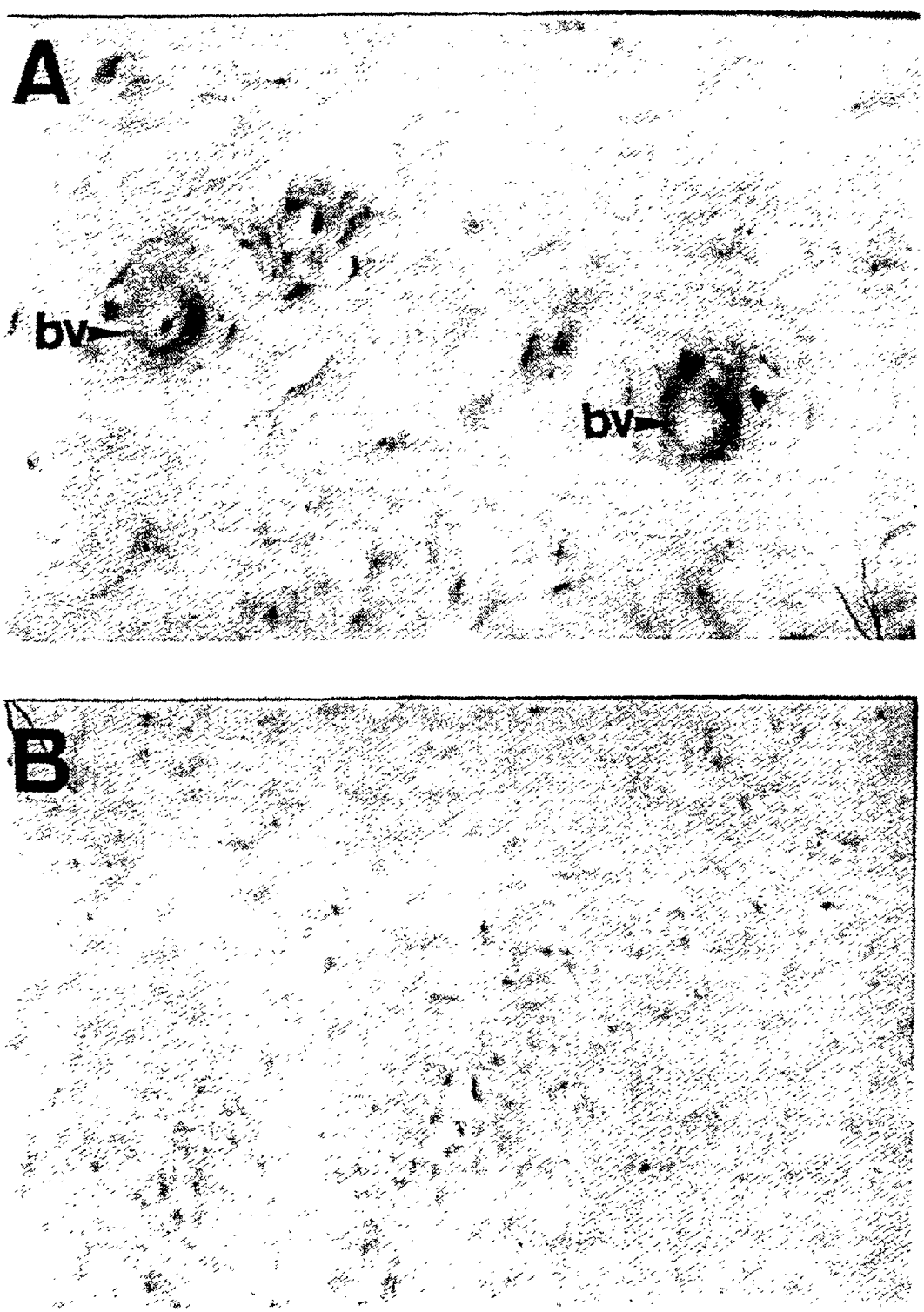
FIG. 3A is an autoradiograph showing staining to VEGF in the vascular smooth muscle layer of cervical blood vessels (bv) in a cervical tissue sample which had been treated with a rabbit polyclonal antibody raised against human VEGF as a primary antibody followed by amplification using a goat anti-rabbit secondary antibody.
FIG. 3B is a comparative autoradiograph obtained using normal rabbit serum instead of the primary, VEGK-specific rabbit antibody used for FIG. 3A.

Strong VEGF immunoreactivity was detected in vascular smooth muscle layer of the cervical blood vessels and a diffuse staining was seen in some elements of the cervical connective tissue such as fibroblasts and mast cells (FIG. 3A). Cervical glands and the crypts showed no staining to VEGF (data not shown). In control sections, no staining was seen using normal rabbit serum instead of primary antibody (FIG. 3B).

PAF-R mRNA Expression

Figure 4:
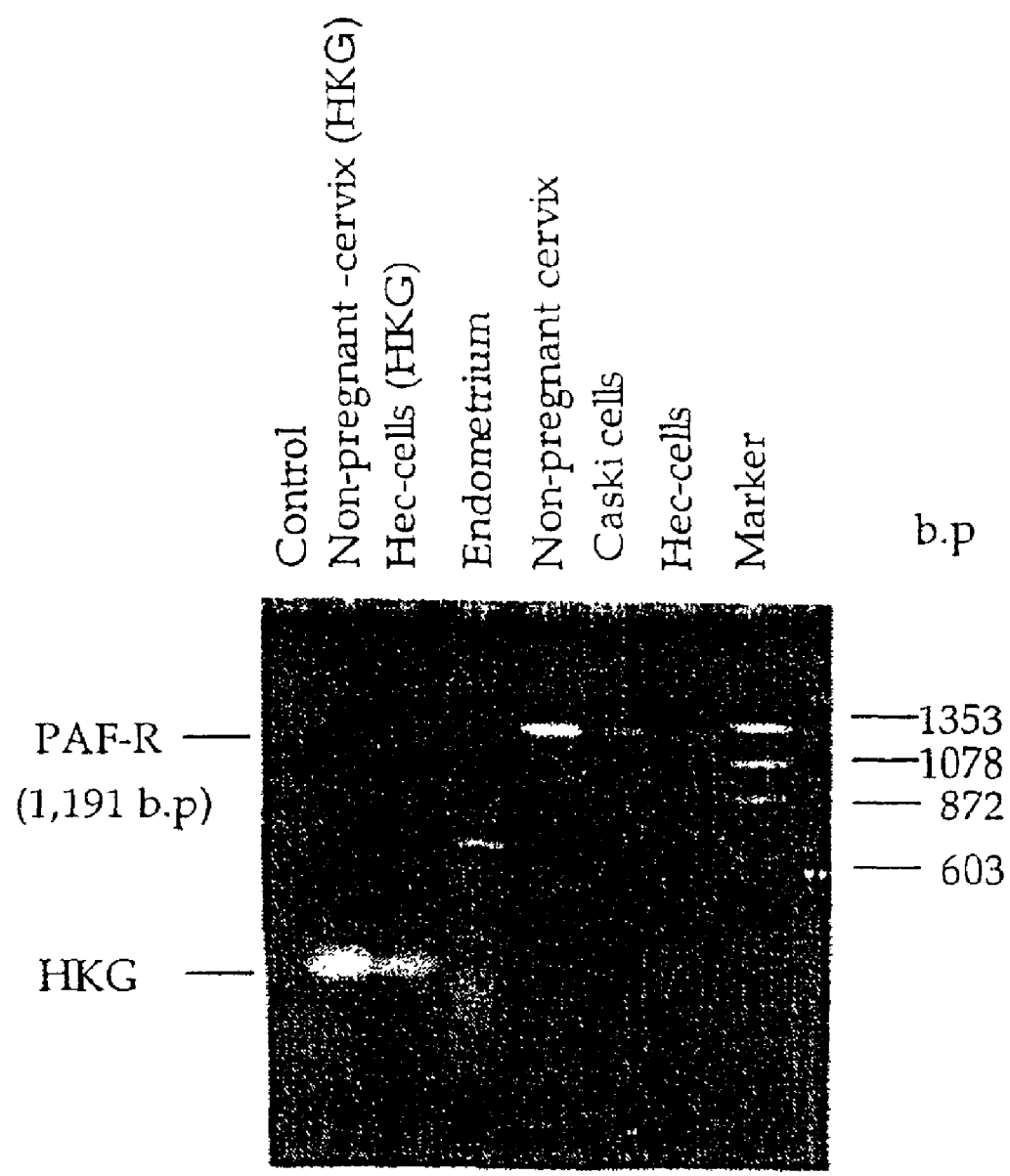
FIG. 4 shows products separated by agarose gel electrophoresis of reverse transcriptase-polymerase chain reaction (RT-PCR) amplification of cDNA generated from Hec-cells, Caski cells (a cervical carcinoma epithelial cell line), a non-pregnant cervix, an endometrium and a negative control (no input of cDNA). The sizes of the PAF-R transcript are shown in base pairs (b.p.). Primers to an HKG (housekeeping gene) were used for the control reactions. FX174/Hae (–72–1353 b.p.) was used as a molecular marker.

Total RNA from non-pregnant cervix was reverse transcribed and subjected to 30 rounds of amplification by PCR using PAF-R sense and an antisense primers. FIG. 4 shows an agarose gel indicating the products of reverse transcriptase-polymerase chain reaction (RT-PCR) amplification of cDNA generated from Hec-cells, Caski cells (a cervical carcinoma epithelial cell line), a non-pregnant cervix, an endometrium and a negative control (no input of cDNA). RNA was reversed transcribed using PAF-R specific primers and amplified for PAF-R. The sizes of the PAF-R transcript is shown in b.p. Primers to a HKG (House keeping gene) were used for the control reactions. Molecular marker is $_\Phi$X174/Hae (−72–1,353 b.p).

PAF-R mRNA Localization

Figure 5:
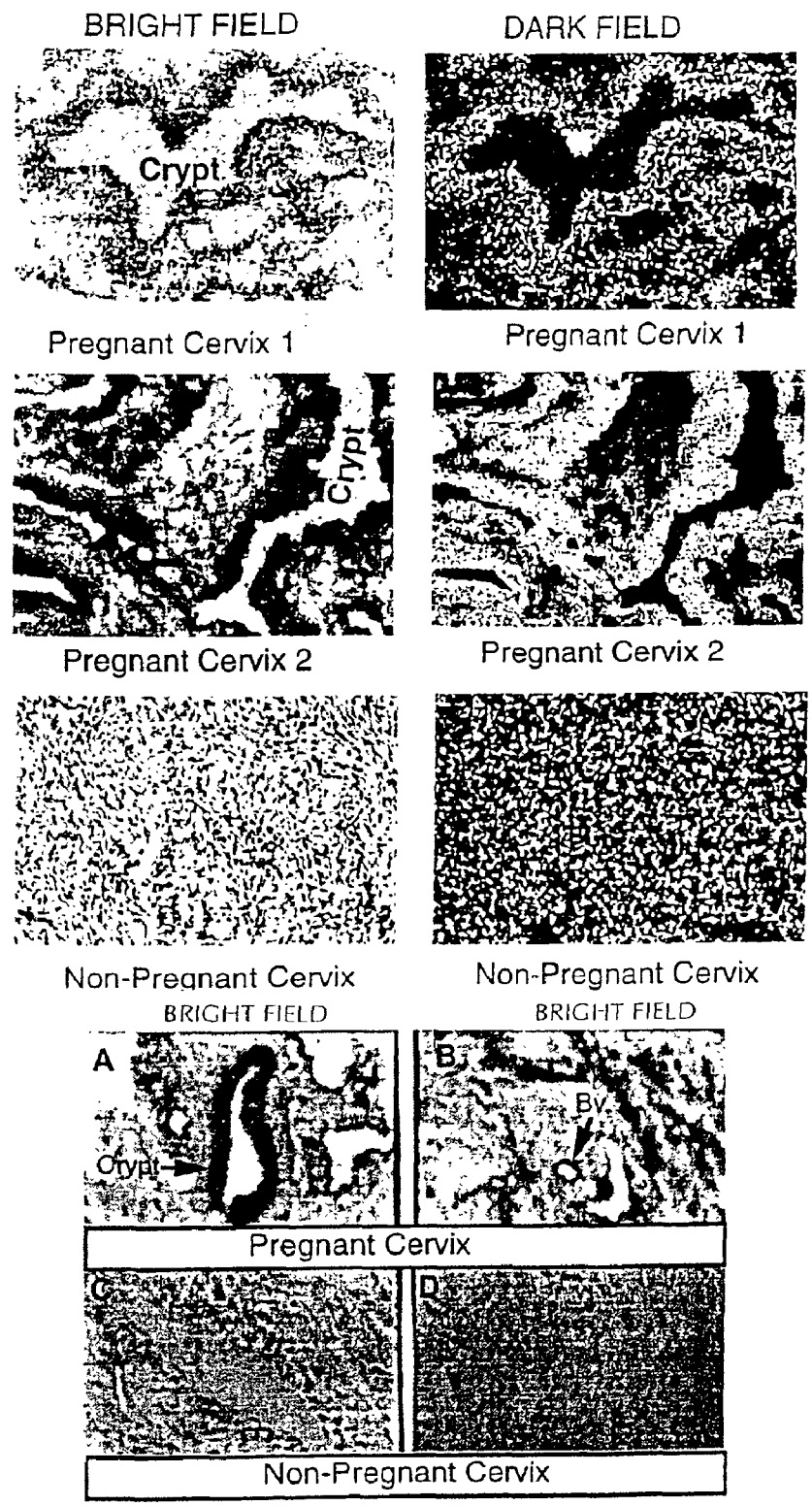
FIG. 5 shows various bright and dark field microphotographs illustrating the degree of PAF-R mRNA localisation around the epithelial cells of the crypts and around the cervical blood vessels (Bv) in pregnant and non-pregnant human cervix.

In order to identify the site of expression of PAF-R mRNA, in situ hybridisation was carried out on samples of both pregnant and non-pregnant cervices. FIG. 5 shows bright field and dark field microphotograph of PAF-R mRNA. Intense expression of PAF-R mRNA was demonstrated in the epithelial cells lining the crypts and around the cervical blood vessels in pregnant cervix. There was apparent lack, or very low levels, of hybridisation signal in the non-pregnant cervix (see FIGS. 5C and D).

Further experimental work in relation to the present invention is described below:—

Source of Tissue:

Human uterine non-pregnant cervix tissue was obtained from non-malignant hysterectomies. The samples were maintained in phenol red free culture media DMEM supplemented with penicillin (1%), streptomycin (1%) and L-Glutamine (1%) and transferred to the laboratory on ice. The biopsies were washed in ice-cold saline solution then cut into small sections 1 to 2 mm and incubated in the above culture medium in 60×15 mm petri dishes at 37° C. in 5% $CO_2$/95% air. Progesterone ($P_2$) was added to the culture medium at concentrations of $10^{-4}$, $10^{-6}$ and $10^{-8}$ M. $17_{-\beta}$ Estradiol ($E_2$) was added to the culture medium either alone at concentrations of $10^{-6}$, $10^{-7}$ and $10^{-8}$ M or for 2 hours to prime the cervical explants at a concentration of $10^{-7}$ M, followed by addition of Progesterone ($P_2$) at concentrations ranging from $10^{31\ 4}$ to $10^{-8}$ M. The effect of $VEGF_{165}$ (1, 10, 50, 100, 200 ng/ml) and PAF ($10^{-6}$–$10^{-10}$ M) in the non-pregnant cervical explants was also investigated. This culture system was chosen because it allows study of the intact tissues in their own matrix and avoids the potentially artefact-producing procedures of cell dispersion and culture. In this system, the cells remain intact for at least 5 days.

Western Blot Analysis:

Cervical tissue, after having been stimulated with $VEGF_{165}$ or PAF for 24 hours or with the ovarian steroid hormones, $17_\beta$-estradiol ($E_2$) and progesterone ($P_2$), for 48 hours, was washed twice in ice-cold PBS and homogenised in ice-cold, high salt lysis buffer (containing 0.4 M KCl, 20 mM HEPES, 1 mM DTT, 20% glycerol, 0.5 mg/ml Bacitracin, 40 $\mu$g/ml PMSF, 5 $\mu$g/ml Peptastin, 5 $\mu$g/ml Leupeptin). Homogenates were centrifuged at 12,000 revolutions/min for 15 minutes and the supernatants containing extracted protein were collected. The culture medium used to incubate the tissue with or without $E_2$, $P2$ or $E_2+P_2$ was also collected, centrifuged. To the supernatant, 3 volumes of ethanol were added and stored at −70° C. for at least 5 hours. Then, the culture medium/ethanol suspension was centrifuged at 10,000 rpm for 10 min and the pellet containing the protein was resuspended in lysis buffer. Total protein, extracted from both tissue and medium, was quantified with the Bio-Rad protein assay, and 500 ng of protein from each sample was diluted in loading buffer (containing 0.02 M Tris-HCl, 0.002 M EDTA, 2% SDS, 10% mercaptoethanol, 20% glycerol, bromophenol blue). Samples were subjected to electrophoresis in a 12% polyacrylamide gel with 5% stacking gel and transferred overnight at 36V onto a nitrocellulose membrane. The membrane was blocked at RT with 1% skimmed milk in Tris-buffered saline solution before incubation with an antiserum (diluted 1:500) directed against the rabbit $VEGF_{165}$ at 4° C. After a 15 min. wash and 2×5 min. washes with Tris-buffered saline solution at room temperature (RT), the membrane was incubated in an anti-rabbit secondary Ab conjugated to alkaline phosphatase. In case of Western blotting experiments for Connexin-43, the membrane was blocked overnight at 4° C. in blocking buffer (1% BSA in 10 mM Tris pH 7.5, 100 mM NaCl, 0.1% Tween 20), before incubation with a monoclonal antibody directed against Connexin-43 again overnight at 4° C. After a 6×5 min. washes with Tris-buffered saline solution, the membrane was incubated in a mouse secondary Ab conjugated to alkaline phosphatase. A chemiluminescence system (ECL-Amersham) was used to visualise the presence of $VEGF_{165}$, Connexin-43 or Flt-1 protein. This is a highly sensitive and quantitative assay for detecting proteins immobilised on membranes.

Northern Blot Hybridisation

RNA (40 $\mu$g/lane) was loaded onto a 1.2% agarose/formaldehyde gel, electrophoretically separated, transferred onto Hybond nylon membranes, and immobilised by exposure to U.V. light for 5 min. Membranes were prehybridized at 42° C. for 8 hours in a solution containing 50% formamide, 5×SSC, 5×Denhardt's solution, 0.5% SDS and salmon sperm DNA at 150 $\mu$g/ml. The $VEGF_{165}$ cDNA was labelled with [$\alpha$-$^{32}$P]dCTP by random-primer extension. 18s oligonucleotide probe labelled by $T_4$ polynucleotide kinase with [$_\beta{}^{32}$P]ATP was used to determine the relative amount of RNA loaded in each lane by rehybridizing the blots that have previously been probed with $VEGF_{165}$. Hybridisation was done under the same conditions with the labelled probe for 18 hours at 42° C. The membrane was washed at 1×SSC, 0.1% SDS for 15 min at RT, in 0.5×SSC, 0.1% SDS for 15 min at RT, and exposed to an intensifying screen cassette at −70° C. for 2 days.

Figure 6:
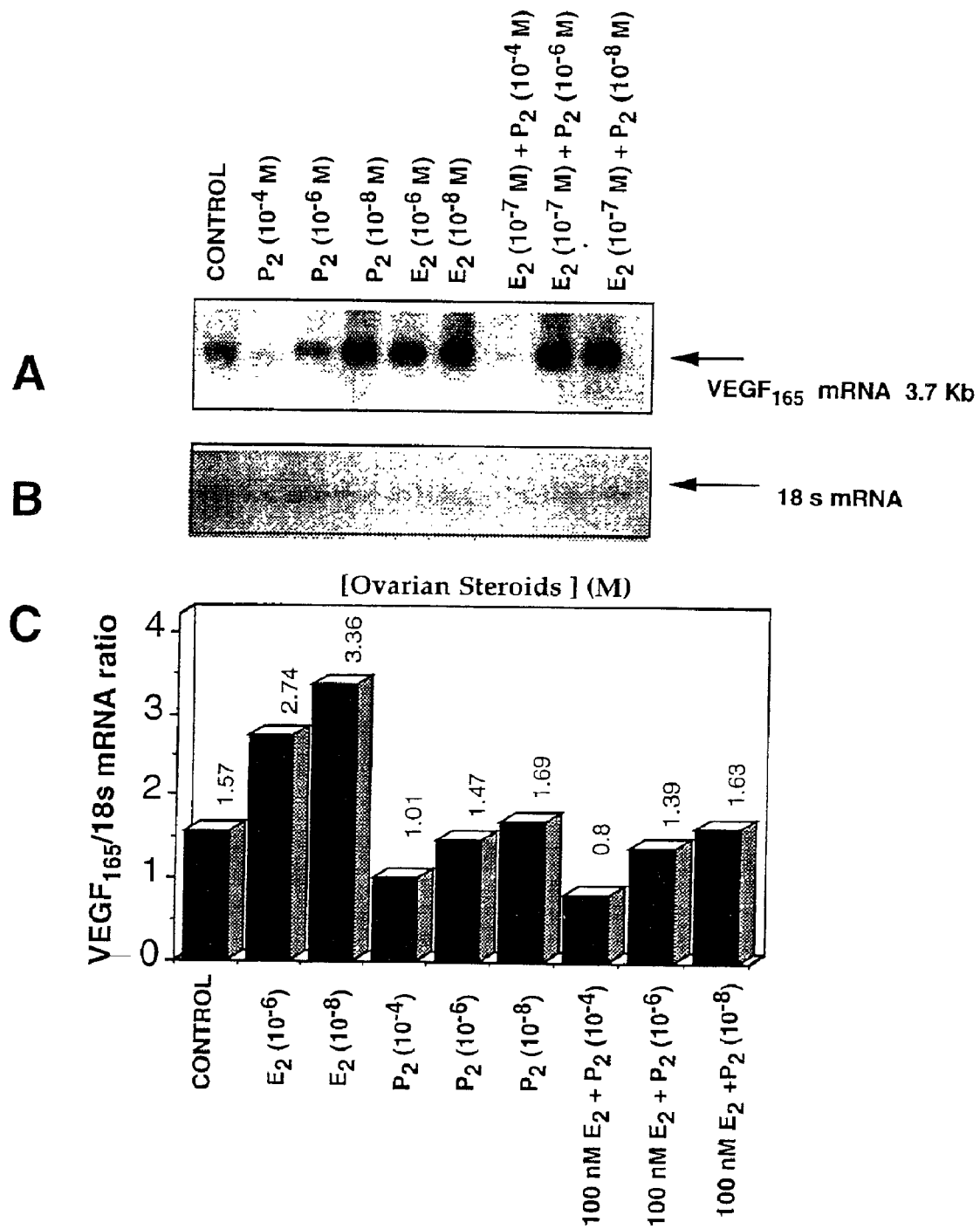
FIG. 6A is an autoradiographic picture obtained upon Northern blot hybridisation showing the effect of the ovarian steroid hormones, $17\text{-}\beta$ Estradiol ($E_2$) and Progesterone ($P_2$), at various concentrations on $VEGF_{165}$ mRNA in non-pregnant cervix.
FIG. 6B is an autoradiographic picture obtained upon Northern blot hybridisation showing, for comparison of RNA loadings, an 18s rRNA oligonucleotide probe hybridised to the same filter.
FIG. 6C is a bar chart showing $VEGF_{165}/18s$ mRNA ratios for the various concentrations of the ovarian steroid hormones used for FIG. 6A, FIGS. 7A and 7b are Western blots showing the effect of the ovarian steroid hormones, $17\text{-}\beta$Estradiol ($E_2$) and Progesterone ($P_2$), at various concentrations on VEGF protein expression in media of non-pregnant cervical explants.

Cervical tissue explants in culture medium were exposed to various concentrations of the ovarian steroid hormones, $17_\beta$-estradiol ($E_2$) and progesterone ($P_2$), for 48 hours, followed by extraction of mRNA from the tissue. Northern blot analysis shows that $17_\beta$-estradiol up-regulates VEGF compared to Control, whereas progesterone at $10^{-4}$ M down-regulated VEGF mRNA as did progesterone at $10^{-4}$ M in the presence of $10^{-7}$ M $17_\beta$-estradiol (FIG. 6A). For comparison of RNA loading, an 18s rRNA oligonucleotide probe was hybridised to the same filter (FIG. 6B). The above up-regulation and down-regulation effects are shown in the bar chart of the densitometric analysis of VEGF abundance relative to 18s mRNA (FIG. 6C).

Figure 7:
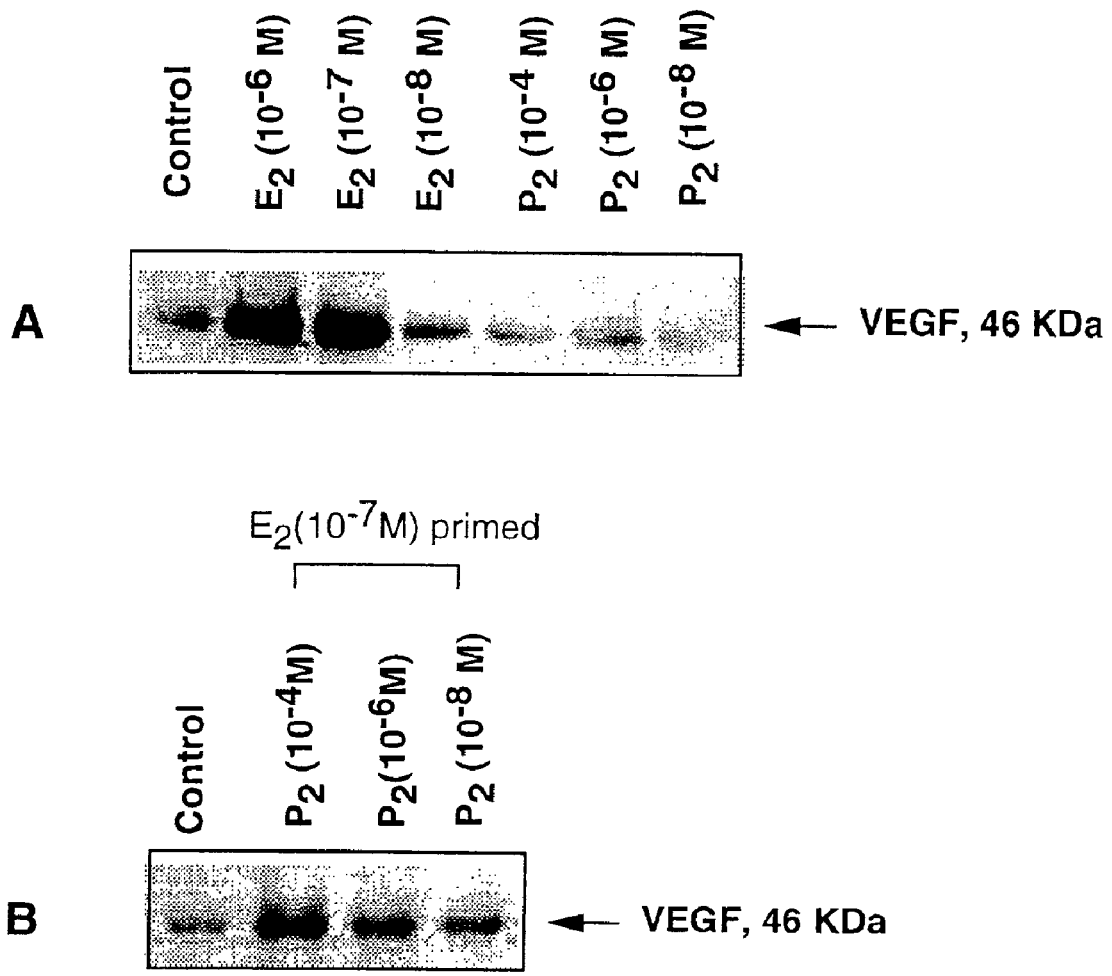

Cervical tissue explants in culture medium were exposed to various concentrations of the ovarian steroid hormones, $17_\beta$-estradiol ($E_2$) and progesterone ($P_2$), for 48 hours, followed by extraction of protein from the tissue as well as the culture medium. Western blot analysis shows that $17_\beta$-estradiol up-regulates the secreted forms of VEGF in the culture medium. In the tissue itself, $17_\beta$-estradiol had no effect, suggesting that the secreted isoforms were affected by $17_\beta$-estradiol. In contrast, progesterone at $10^{-4}$ M down-regulated VEGF both in the culture medium and in the tissue itself as compared with the Control. (FIG. 7A).

When the in vivo situation was mimicked by priming the cervical explants with $17_\beta$-estradiol for 4 hours prior to addition of progesterone, the increasing concentration of progesterone caused a dose-dependent increase in VEGF protein expression both in the culture medium and the tissue. (FIG. 7B).

Figure 8:
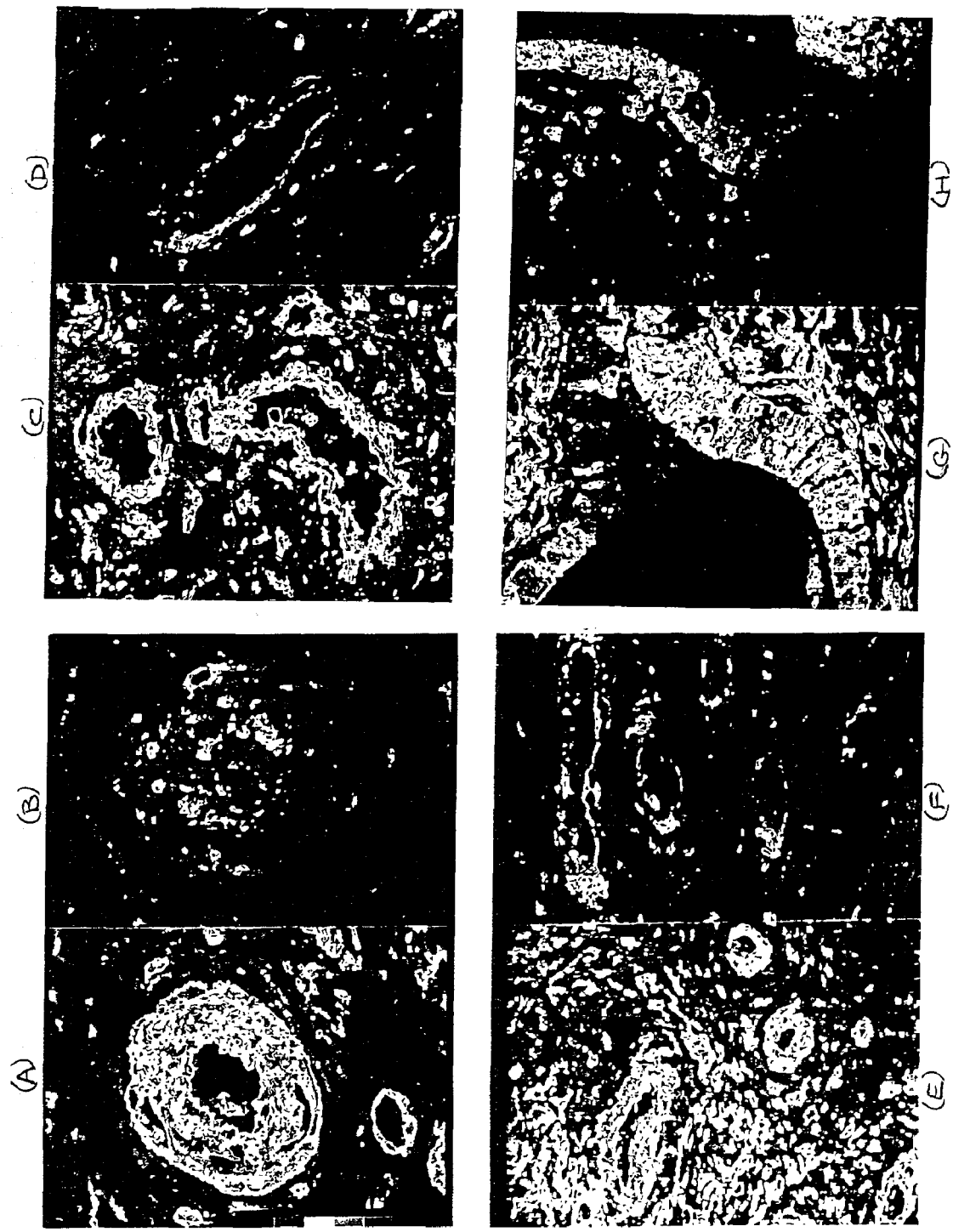
FIGS. 8A to 8H are autoradiographs showing high localisation of VEGF in the artery, vein, capillary and crypt of the pregnant cervix as compared to the non-pregnant cervix.
Figure 9:
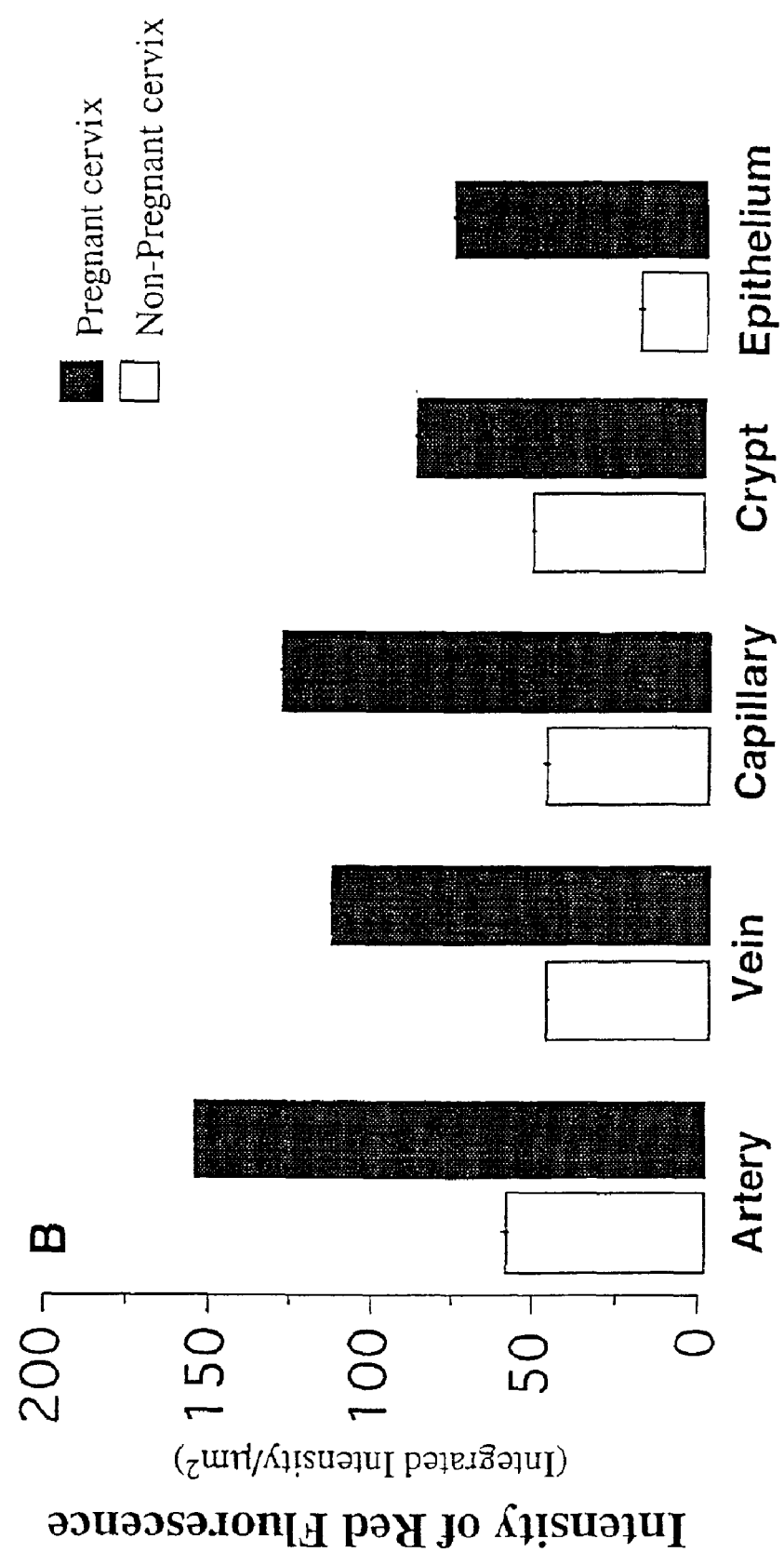
FIG. 9 is a bar chart showing the effects illustrated in FIGS. 8A to 8H.

Using a fluorescent label, alkaline phosphatase-Fast Red method, we have shown that VEGF is highly significantly localised in the media of pregnant cervical blood vessels as compared to the non-pregnant cervix. The red reaction product of alkaline phosphatase immuno-conjugates produces a brilliant red fluorescence that is visible by fluorescence microscopy using both fluorescent and rhodamine filter combinations. The fluorescence properties of the reaction product allows quantitation by image analysis using confocal microscopy. FIGS. 8A and 8B show an artery in pregnant and non-pregnant cervix, respectively. FIGS. 8C and 8D show a vein in pregnant and non-pregnant cervix, respectively. FIGS. 8E and 8F show a capillary in pregnant and non-pregnant cervix, respectively. FIGS. 8G and 8H show a crypt in pregnant and non-pregnant cervix, respectively. These effects are graphically shown in FIG. 9 which also includes comparative data on the epithelium in pregnant and non-pregnant cervical tissue.

Figure 10:
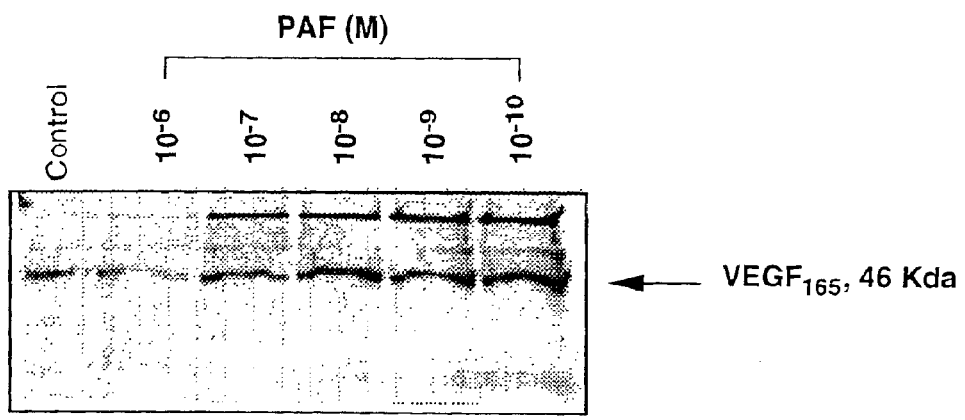
FIG. 10 is a Western blot analysis showing the effect of PAF at various concentrations on VEGF expression in non-pregnant cervix as detected.

FIG. 10 shows the effect of PAF on VEGF expression in non-pregnant cervix as detected by the above-described Western blot analysis. As can be seen from FIG. 10, PAF is another potent inducer of vascular permeability and also increases VEGF expression.

Figure 11:
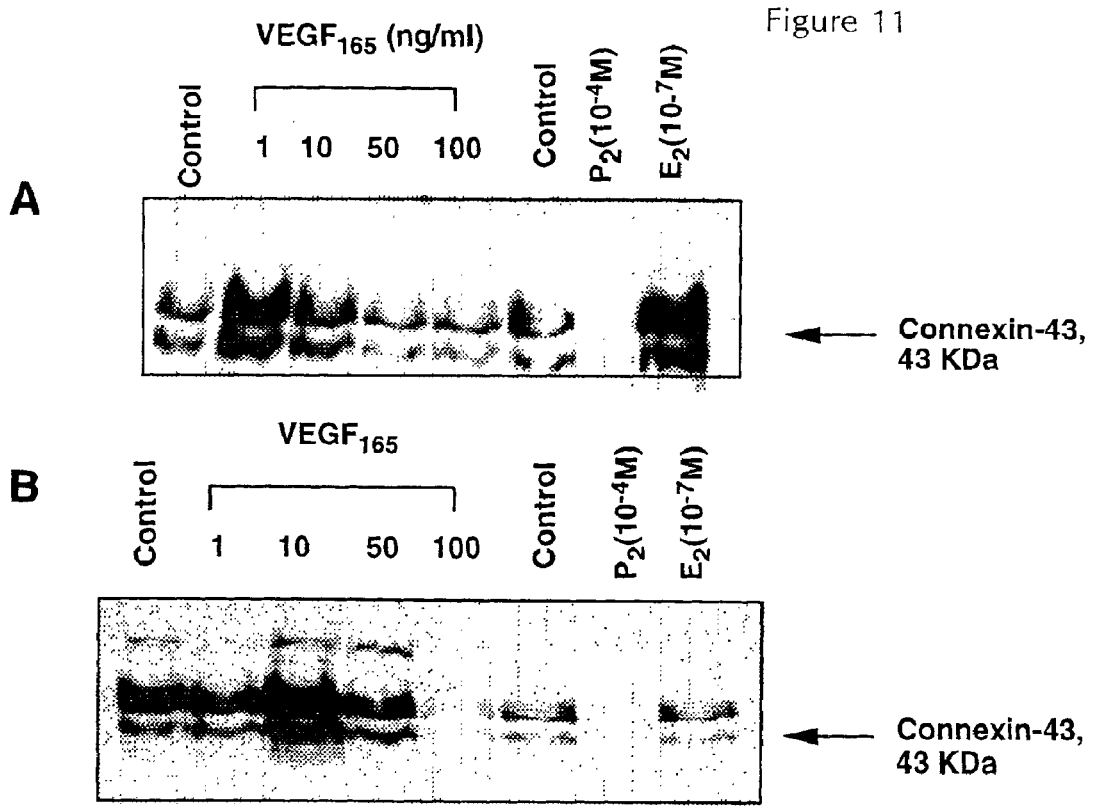
FIGS. 11A and 11B are Western blots showing the effect of $hrVEGF_{165}$ and the ovarian steroid hormones, $17\text{-}\beta$ Estradiol ($E_2$) and Progesterone ($P_2$), at various concentrations on Connexin-43 expression in non-pregnant myometrial (FIG. 11A, n=2) and non-pregnant cervical (FIG. 11B, n=2) explants.
Figure 12:
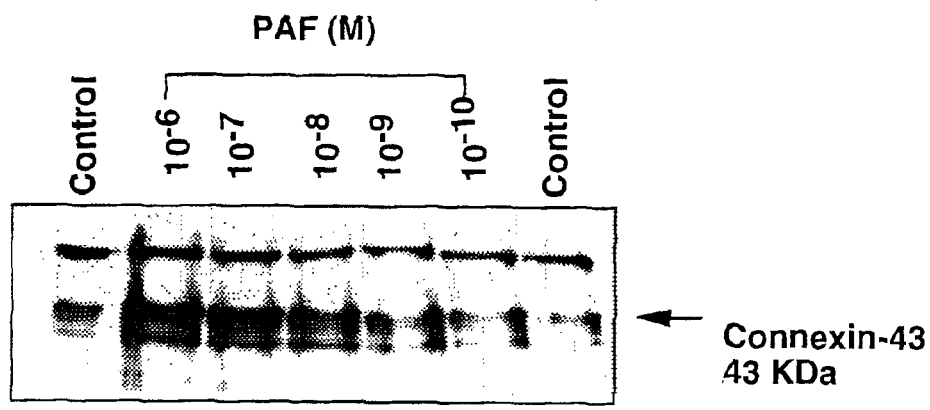
FIG. 12 is a Western blot showing the effect of PAF at various concentrations on Connexin-43 expression in non-pregnant cervix.

FIGS. 11A and 11B respectively show the up-regulation of connexin-43 expression by VEGF in myometrial and cervical explants. FIG. 12 shows the up-regulation of connexin-43 expression in cervix. Gap junctions are proteinaceous pores connecting cells which allow passage of ions and other small molecules from one cell to another, allowing cell-to-cell communication. Tyrosine phosphorylation of connexin-43, a 43 kDa isoform of gap junction protein, has been shown to inhibit transport through the gap junction. In late pregnant guinea pigs, increase in the density of gap junctions as demonstrated immunocytochemically by a dramatic increase in connexin-43 in the myometrium following treatment with antiprogestins, supports the role of these structures as sites of propagation and the basis for synchrony during labour. VEGF may promote labour as well as induce cervical ripening by increasing cell-to-cell communication.

Figure 13:
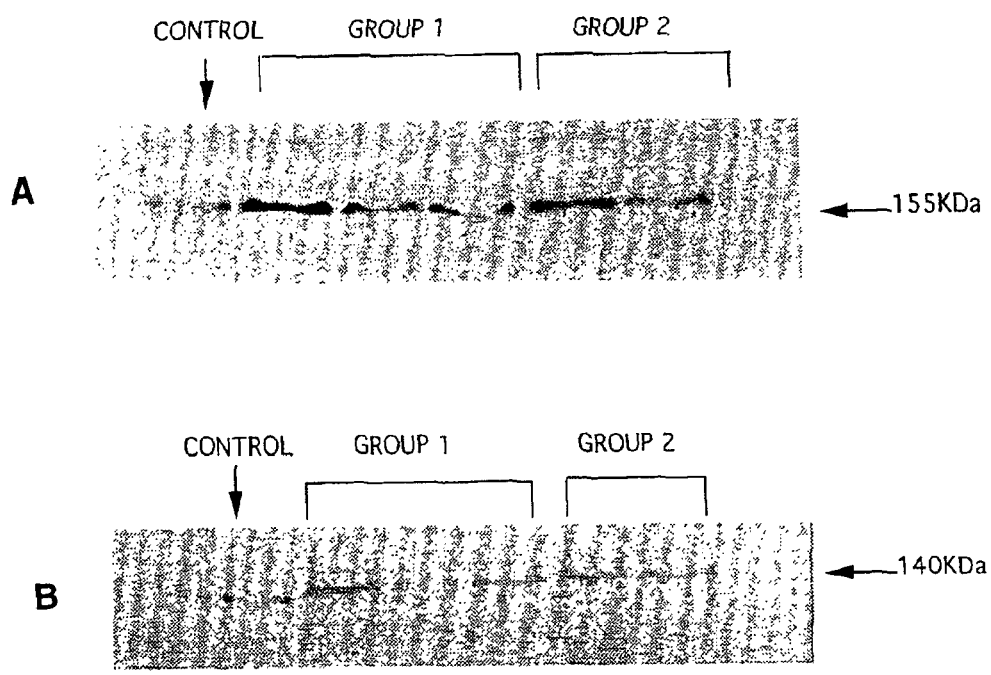
FIGS. 13A and 13B are Western blots showing brain cNOS (FIG. 11A) and endothelial cNOS proteins (FIG. 11B) from human myometrium collected after elective Caesarean section (ie non-labouring myometrium, Group 1, n=3) and emergency Caesarian section (ie labouring myometrium, Group 2, n=2), both at term delivery.

Nitric oxide is believed to maintain a quiescent state in the myometrium during pregnancy and labour, and animal studies have shown that, at the time of labour, nitric oxide levels drop to allow increased myometrial cell activity. We have shown that there is no difference in nitric oxide synthase (NOS) immunoreactivity between labouring and non-labouring myometrium by ECL Western blot analysis (FIG. 13). We have shown that nitric oxide donors decrease and inhibitors of NOS increase both VEGF in the cervical explants, and thus it is considered that the use of a nitric oxide donor, e.g. glycerol trinitrate (GTN), can inhibit cervical ripening by decreasing VEGF expression. It is therefore proposed to administer a nitric oxide donor, e.g. GTN, intravaginally to delay the onset of labour.

Patient Treatment Regimes

The invention proposes to treat patients in one of the following ways:—
(1) Instillation directly into the cervical canal or intravaginally using vehicles such as water-soluble gels or slow-releasing resins.
(2) Intravenous infusion, which may be the preferred method of treatment.
(3) As a pellet inserted directly under the skin using a long-acting, near-zero order releasing system.
(4) By oral administration of the drug.

A safe and effective delivery implies concerted changes in uterine activity and cervical function. The uterus shifts from a relative state of quiescence during most of pregnancy to develop rhythmic and forceful contractions during labour. On the other hand, the cervix, which normally remains long and closed during pregnancy, undergoes morphological, biochemical, and physical changes (ripening), which allow it to open (dilate) before the passage of the fetus. In pregnancies complicated by preterm labour or in dystocic deliveries these events lack in synchronicity. Attempts to modulate cervical changes independently of uterine activity become valuable as the cervix is not a passive bystander in the parturition process. VEGF is an essential element in the cascade of events leading to cervical ripening and dilation. This has been demonstrated using an in vivo animal model of cervical ripening. It is considered that the animal in vivo model will be indicative of the effects obtained with pregnant women.

Methodology: Animals: Times pregnant nuliparous Sprague-Dawley rats (Harlan Laboratories) were used. Drugs were administrated intra-vaginally dissolved in 2% methylcellulose gel under two protocols.

Protocol A: 0.2 ml gel (in AM and PM) from day 12 to day 16 of pregnancy (a total of 8 applications). On day 16 the animals were sacrificed, the cervix isolated and tested for mechanical extensibility properties.

Figure 14:
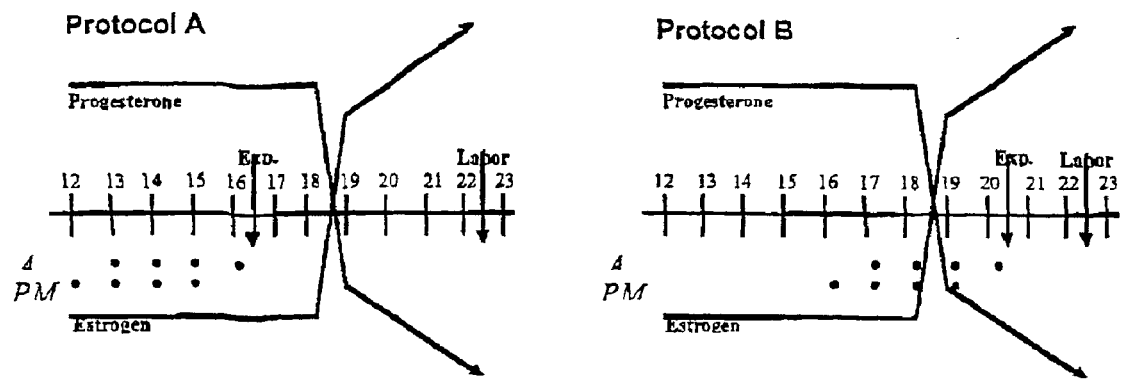
FIG. 14 is a schematic representation of two experimental protocols to investigate the effect of VEGF administration on the extensibility of rat cervix.

Protocol B: 0.2 ml gel applications are performed twice daily from day 16 to day 20 and animals were sacrificed on day 20 (FIG. 14).

Treatments (Protocols A and B): Mouse recombinant $VEGF_{164}$ (the murine equivalent of human $VEGF_{165}$) was dissolved at a concentration of 10 and 100 ng/ml gel. Control animals received applications of gel only. Some animals were injected on day 19 s.c. with 10 mg progesterone receptor antagonist RU486, a protocol which induces in 24 h preterm delivery in 80% of animals.

Figure 15:
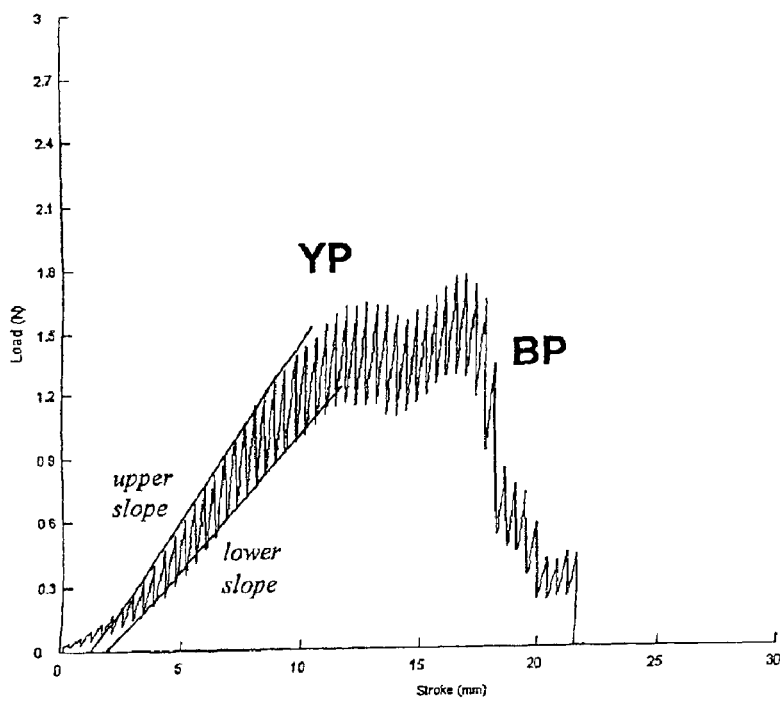
FIG. 15 is a representative stress-strain curve for a rat cervix showing the yield point (YP) and the break point (BP)

The tensile properties of the isolated cervix were evaluated using the Shimadzu EZ-Test instrumentation using a test regimen which mimicked the conditions during labour. Briefly, the cervix was suspended between two hooks by means of threads passed through the cervical canal. It was then placed in a 40 ml tissue bath containing 10 mM HEPES/PBS solution (pH=7.4) maintained at 25° C. At this temperature spontaneous contractility within the cervix is inhibited and contractions do not interfere with the extensibility measurements. Each cervix was allowed 30 min. to equilibrate. The lower hook was fixed while the upper hook was movable, to simultaneously record displacement and force with a sample rate of 20 Hz. These data were transmitted to a personal computer to further analyze the generated on-line stress-strain curves and regression parameters. The upper hook was moved until a small resistance of the tissue (20 mN) was recorded after which the tester automatically moved the upper hook to incrementally stretch the cervix in steps of 0.4 mm. at 1 min. intervals. Between subsequent stretches the hook rested for 1 min. allowing the cervix to accommodate. During the accommodation periods the cervix reverted back to a relaxed state, therefore diminishing the opposed resistance and thus the tension recorded by the tester. FIG. 15 illustrates a typical stress-strain plot of a rat cervix. The moment at which the increase in strain does not produce any increase in stress is described as the yield-point (YP). At YP permanent morphological changes and breaks in the material begin to occur. Break-point (BP) is the moment where the tissue completely breaks and the load abruptly falls toward zero. To quantify the elastic behaviour of the cervix (cervical resistance), straight lines are fitted through the linear portion of the force versus displacement curve. The slopes of the upper, lower and mid-point regression lines that are related to Young's modulus for elastic materials were used to best characterise the tensile properties of the sample. A larger slope indicates a higher resistance to dilation, therefore lower extensibility.

Figure 16:
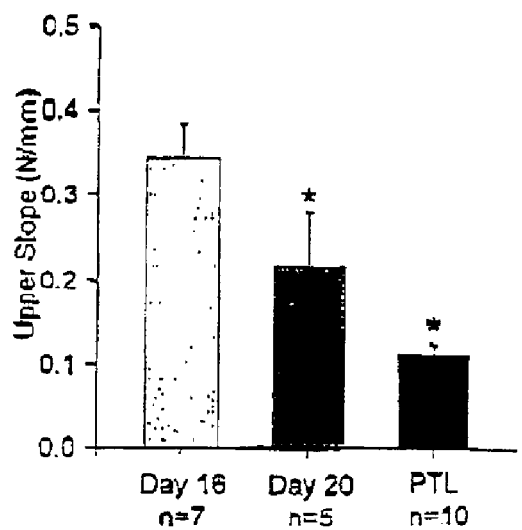
FIGS. 16 and 17 are charts of upper slope values taken from rat cervix stress-strain curves under various treatment regimes.
Figure 17:
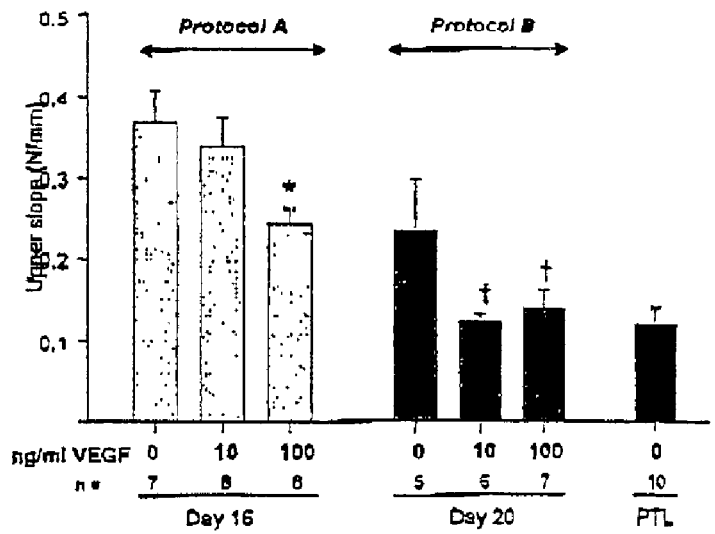

During gestation there was a significant decrease in slope. Dilated cervices collected during preterm delivery (at least one pup protruded through a cervical canal) had an even lower slope although not statistically different from day 20 (p=0.071) (FIG. 16). Treatment with 10 ng/ml VEGF induced a statistically significant decrease in slope only when applied later in pregnancy (protocol B), while 100 ng/ml VEGF gel significantly increased cervical extensibility in both experimental protocols. The level to which 100 ng/ml VEGF decreased the slope on day 20 was similar to that seen in dilated cervices, during active labour (FIG. 17). There were no differences in fetal or placental weights among treatment for a given gestational age.

The above experiment demonstrates that $VEGF_{164}$ promotes cervical ripening when applied locally to live pregnant animals. Additional experiments showed that the increased extensibility of the cervical tissue is accompanied by increased protein glycans, a marker for hydration, indicating that the increased extensibility is due at least partly to the increased vascular permeability induced by VEGF.

Figure 18:
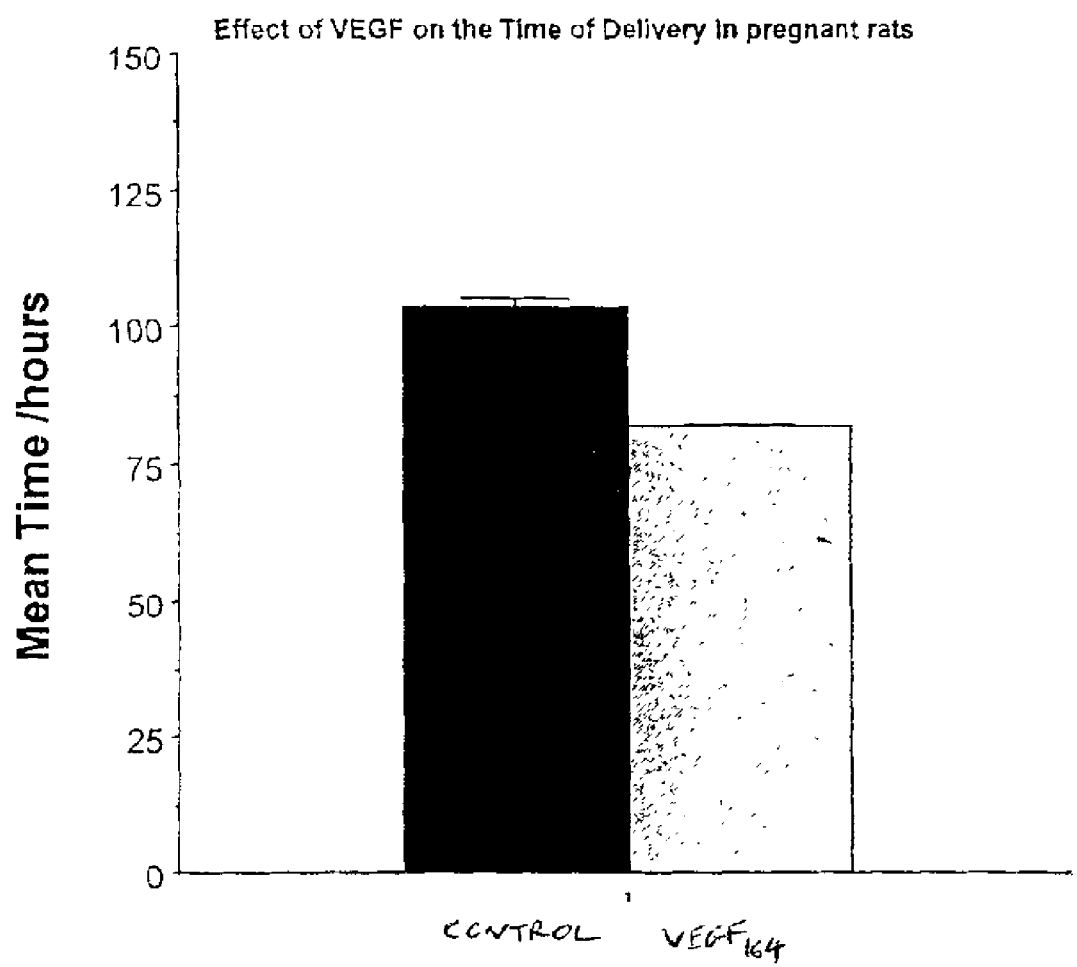
FIG. 18 is a chart showing the reduction in time for the onset of delivery for rats after treatment with VEGF.

In a separate, but related set of experiments, it was shown that administration of $VEGF_{164}$ (100 ng/ml gel: protocol B) significantly hastened the onset of delivery. The mean delivery time for the first pup in the control group was 103.8 (sem+0.85) hours while the $VEGF_{164}$-treated rats delivered early at 81.85 (sem+0.33) hours (p<0.0001). This effect is illustrated gradually in FIG. 18.

Having established that administration of VEGF has a significant effect on cervical ripening and the onset of delivery, the effect of agents which inhibit VEGF activity were also investigated.

Administration of VEGF binding protein sFlt-1 (also known as sm-sFLT-1(D1-6)-IgG) when given at a dose of 2.5 mg/kg twice daily from day 16 delayed cervical ripening. The stress-strain curve had a steeper slope up to the yield point and was significantly different to the normal day 20 curve between the yield point and the breaking point. Both these features were interpreted as indicating the cervical tissue to be less extensible and more rigid—i.e. less ripe. It is considered that additional experiments will show that administration of sFlt-1 will delay the onset of labour.

I claim:

1. A method of hastening cervical ripening comprising administering to a patient a pharmaceutically effective amount of an agent for increasing vascular permeability within the cervix, said agent being selected from the group consisting of vascular endothelial growth factor $(VEGF)_{121}$, $VEGF_{145}$, $VEGF_{165}$, $VEGF_{189}$, $VEGF_{206}$, a biologically active VEGF fragment, and placenta growth factor (PlGF).

2. The method according to claim 1, wherein said administration is topical, either intra-vaginally or directly into the cervical canal.

* * * * *